(12) United States Patent
Barnett et al.

(10) Patent No.: US 12,347,563 B2
(45) Date of Patent: Jul. 1, 2025

(54) SYSTEM AND METHOD FOR ASSESSING PHYSIOLOGICAL STATE

(71) Applicant: Cambridge Cognition Limited, Cambridgeshire (GB)

(72) Inventors: Jennifer Helen Barnett, Cambridgeshire (GB); Francesca Kathleen Cormack, Cambridgeshire (GB); Nicholas Theodore Taptiklis, Cambridgeshire (GB); Merina Tong Su, Cambridgeshire (GB)

(73) Assignee: Cambridge Cognition Limited, Cambridgeshire (GB)

( * ) Notice: Subject to any disclaimer, the term of this patent is extended or adjusted under 35 U.S.C. 154(b) by 0 days.

(21) Appl. No.: 16/758,729

(22) PCT Filed: Oct. 24, 2018

(86) PCT No.: PCT/GB2018/053062
§ 371 (c)(1),
(2) Date: Apr. 23, 2020

(87) PCT Pub. No.: WO2019/081915
PCT Pub. Date: May 2, 2019

(65) Prior Publication Data
US 2020/0365275 A1    Nov. 19, 2020

(30) Foreign Application Priority Data
Oct. 24, 2017   (GB) .................................. 1717469

(51) Int. Cl.
*G16H 50/30*     (2018.01)
*A61B 5/00*      (2006.01)
(Continued)

(52) U.S. Cl.
CPC ............. *G16H 50/30* (2018.01); *A61B 5/165* (2013.01); *A61B 5/4803* (2013.01);
(Continued)

(58) Field of Classification Search
CPC ........ G16H 50/30; G16H 10/20; G16H 10/60; G16H 20/70; G16H 50/20; G16H 50/70;
(Continued)

(56) References Cited

U.S. PATENT DOCUMENTS 6,157,913 A * 12/2000 Bernstein ................ G10L 17/26
704/275
9,782,122 B1 * 10/2017 Pulliam .................. A61B 5/1112
(Continued)

FOREIGN PATENT DOCUMENTS

JP  2003210418 A   7/2003
JP  2004240394 A   8/2004
(Continued)

OTHER PUBLICATIONS

Andersson, G. et al., "Effect of cognitive load on postural control," Brain Research Bulletin, Elsevier, 58(1), pp. 135-139 (2002).
(Continued)

*Primary Examiner* — Sheetal R Paulson
(74) *Attorney, Agent, or Firm* — Volpe Koenig

(57) ABSTRACT

A system for assessing the physiological state of a subject, comprising: a task delivery module configured to communicate to a subject at least two sets of information, each set of information relating to a cognitive task requiring a spoken response from the subject; a response detection module configured to record the respective spoken responses from the subject as an audio signal, the response detection module comprising a microphone; an analysis module configured to analyze the audio signals corresponding to the respective spoken responses recorded by the response detection module
(Continued)

Figure 1:
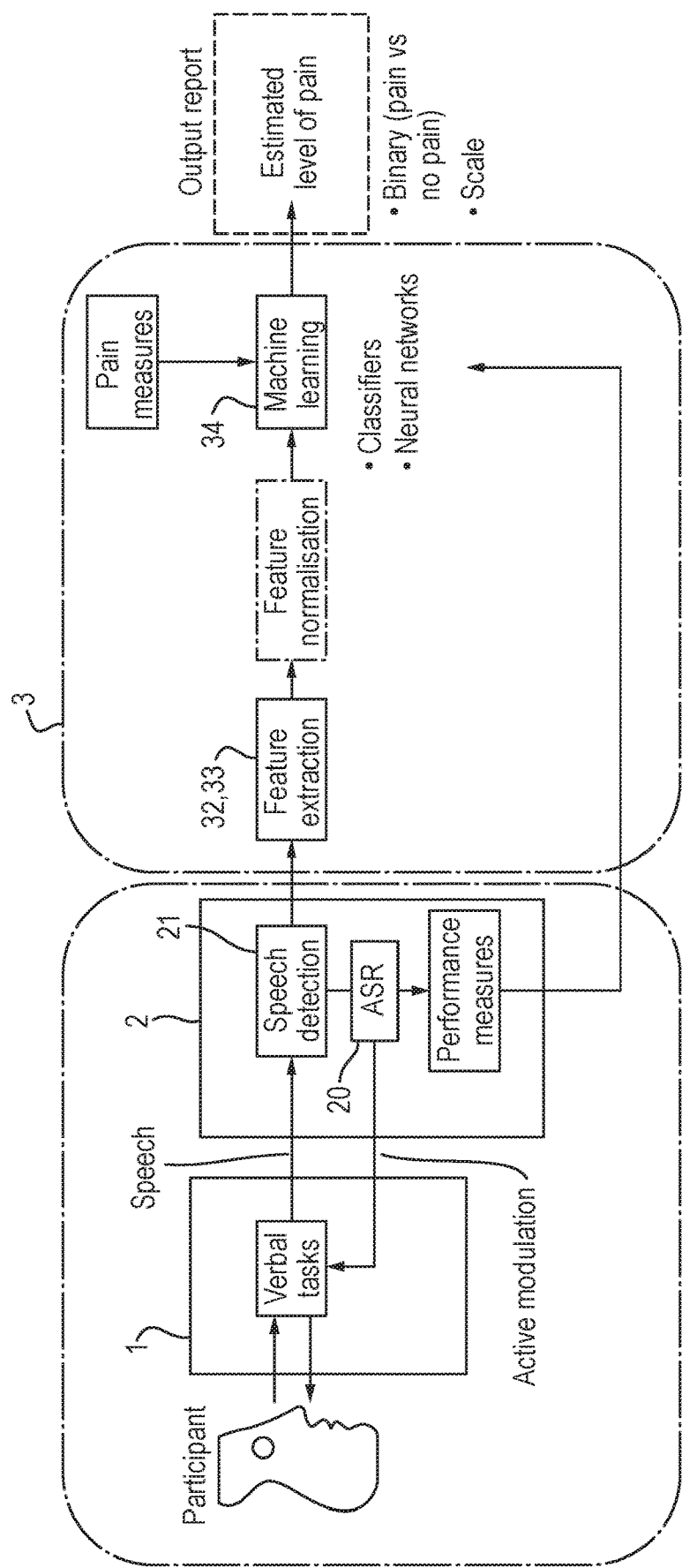

to determine from the respective spoken responses one or more characteristics indicative of the physiological state of the subject, compare said characteristics from the respective spoken responses, and determine the physiological state of the subject based on said comparison.

10 Claims, 5 Drawing Sheets

(51) Int. Cl.
| | |
|---|---|
| A61B 5/16 | (2006.01) |
| G06N 3/08 | (2023.01) |
| G10L 15/16 | (2006.01) |
| G10L 25/63 | (2013.01) |
| G16H 10/20 | (2018.01) |
| G16H 10/60 | (2018.01) |
| G16H 20/10 | (2018.01) |
| G16H 20/70 | (2018.01) |
| G16H 40/20 | (2018.01) |
| G16H 50/20 | (2018.01) |
| G16H 50/70 | (2018.01) |

(52) U.S. Cl.
CPC .......... *A61B 5/4824* (2013.01); *A61B 5/4836* (2013.01); *A61B 5/7264* (2013.01); *A61B 5/7475* (2013.01); *G06N 3/08* (2013.01); *G10L 15/16* (2013.01); *G10L 25/63* (2013.01); *G16H 10/20* (2018.01); *G16H 10/60* (2018.01); *G16H 20/10* (2018.01); *G16H 20/70* (2018.01); *G16H 40/20* (2018.01); *G16H 50/20* (2018.01); *G16H 50/70* (2018.01); *A61B 2503/42* (2013.01)

(58) Field of Classification Search
CPC ..... A61B 5/165; A61B 5/4803; A61B 5/4824; A61B 5/7264; A61B 5/7475; G10L 15/16; G10L 25/63
See application file for complete search history.

(56) References Cited

U.S. PATENT DOCUMENTS

| | | | | |
|---|---|---|---|---|
| 10,978,181 | B2* | 4/2021 | Harper | G16H 50/30 |
| 11,120,895 | B2* | 9/2021 | Shriberg | G16H 20/10 |
| 2009/0124863 | A1 | 5/2009 | Liu et al. | |
| 2011/0207099 | A1* | 8/2011 | Chen | A61B 5/7264 |
| | | | | 434/236 |
| 2012/0116186 | A1 | 5/2012 | Shrivastav et al. | |
| 2015/0064669 | A1 | 3/2015 | Golan et al. | |
| 2016/0125748 | A1 | 5/2016 | Ashford | |
| 2016/0262680 | A1* | 9/2016 | Martucci | A61B 5/4088 |
| 2017/0188979 | A1 | 7/2017 | Volpe | |
| 2017/0251985 | A1* | 9/2017 | Howard | A61B 5/165 |

FOREIGN PATENT DOCUMENTS

| | | |
|---|---|---|
| JP | 2011255106 A | 12/2011 |
| JP | 2012000449 A | 1/2012 |
| JP | 2016166970 A | 9/2016 |
| WO | 2003045252 A1 | 6/2003 |
| WO | 2013/138633 A1 | 9/2013 |
| WO | WO-2016028495 A1 * | 2/2016 ............. A61B 5/165 |

OTHER PUBLICATIONS

Eyben, F., Weninger, F., Gross, F., & Schuller, B., Recent Developments in openSMILE, the Munich Open-Source Multimedia Feature Extractor, In Proc. ACM Multimedia (MM), Barcelona, Spain, ACM, ISBN 978-1-4503-2404-5, pp. 835-838 (2013).
Fusaroli, R. et al., "Is voice a marker for Autism spectrum disorder? A systematic review and meta-analysis," Autism Research, 10(3), pp. 384-407 (2017).
Gurol-Urganci I, de Jongh T, Vodopivec-Jamsek V, Atun R, Car J., "Mobile phone messaging reminders for attendance at healthcare appointments," Cochrane Database of Systematic Reviews 2013, Issue 12. Art. No. CD007458. (2013).
Huang, X., Acero, A. and Hon, H., "Spoken Language Processing: A guide to theory, algorithm, and system development," Prentice Hall (2001).
Johnstone, Tom, PhD Thesis, "The effect of emotion on voice production and speech acoustics," University of Western Australia. Accessed via http://brainimaging.waisman.wisc.edu/~tjohnstone/Thesis.pdf (2001).
Lautenbacher, S. et al., "Phonetic Characteristics of Vocalizations during Pain," Pain Reports, 2(e597), pp. 1-5. (2017).
Marquard, C. et al., "Speak, Think , Act : A phonetic analysis of the combinatorial effects of respiratory mask , physical and cognitive stress on phonation and articulation," MSc Thesis (2017).
Miller-Matero, LR, Clark, KB, Brescacin, C, Dubaybo, H & Willens, DE, "Depression and literacy are important factors for missed appointments," Psychology, Health & Medicine, 21:6, 686-695 (2016).
Nevler, N. et al., "Automatic measurement of prosody in behavioral variant FTD," pp. 1-8 (2017).
Oshrat, Y., "The Fingerprints of Pain in Human Voice," (Thesis, The Open University of Israel Computer Science Division) (2014).
Place et al, Behavioral Indicators on a Mobile Sensing Platform Predict Clinically Validated Psychiatric Symptoms of Mood and Anxiety Disorders. J Med Internet Res. 19(3):e75 (2017).
Tsai, F. S. et al., "Toward development and evaluation of pain level-rating scale for emergency triage based on vocal characteristics and facial expressions," Proceedings of the Annual Conference of the International Speech Communication Association, INTERSPEECH, 8-12-NaN-2016, pp. 92-96. (2016).
Vogel, A. P., Fletcher, J. and Maruff, P., "Acoustic analysis of the effects of sustained wakefulness on speech," The Journal of the Acoustical Society of America. Acoustical Society of America, 128(6), pp. 3747-3756 (2010).
Zhang, H.-H. et al., "Classification of Parkinson's disease utilizing multi-edit nearest-neighbor and ensemble learning algorithms with speech samples," Biomedical engineering online. BioMed Central, 15(1), p. 122 (2016).
The Relationship Between Arithmetic, Forward and Backward Singing in the Weschsler Intelligence Test: a Study of Adults and Children in the Lower Grades of Elementary School; Shukichi Era; Japanese Journal On Support System for Developmental Disabilitites; Developmental Disability Support Systems Research vol. 5 No. 2 2006; pp. 1-6; Mar. 31, 2006.
Cognitive Functions Related To Forward and Reverse Singing; Keitaro Ishijima; Shinshu University Graduate School; pp. 384; Aug. 9, 2015.

* cited by examiner

SYSTEM AND METHOD FOR ASSESSING PHYSIOLOGICAL STATE

This invention relates to systems and methods for assessing the physiological state of a subject. The invention is particularly, but not exclusively, concerned with methods which use results from voice biomarkers and cognitive and/or clinical assessments to better assess physiological state, such as pain, including symptoms of neurological or neuropsychiatric conditions.

Clinical decision making, including diagnosis of neurological and neuropsychiatric disease and prescription of medication, relies on accurate tests of cognitive function and symptom classification. In addition, cognitive testing can play an important role in the management of general brain health in people unaffected by neurological disease. Moreover, cognitive testing may be part of a general fitness assessment with implications for health and safety policy. For example, cognitive testing provides:

- baseline information for a subject to assess risk for a condition or as part of a study providing normative data for a particular population;
- a means to detect early signals of the onset of neurological disorders or their precursors;
- an aid in the accurate diagnosis of neurological disorders;
- a means to monitor the course of neurological disorders; and
- a method to determine the impact that a course of treatment is having on the patient in terms of both cognitive safety and efficacy.

Cognitive testing and clinical assessment typically take the form of a series of discrete tests undertaken by the patient under the supervision of a clinician. Procedures employed during cognitive testing typically take the form of a structured set of standardised puzzles or task that specifically taps into one or more cognitive processes of the brain. The instructions and 'rules' of the test can be delivered in writing, verbally, or through an automated system such as a computer. For example, a patient might be asked to learn a list of words and recall as many words as possible after a set period of time (or after doing a different task). This particular task tests the patient's memory capacities, and is sensitive to symptoms of dementia. Scores calculated based on the patient's responses can be done by a trained human or a computer, in real time or based on a record which may be written, oral, manual, or digital. The tests are scored against previous test data for the patient or against historic data sets for relevant populations with normal cognitive function and those with known neurological disorders. The relevant population may be selected by reference to age, gender and known medical conditions.

Examples of current cognitive function tests for dementia and other neurological disorders include the Mini Mental State Examination, the Abbreviated Mental Test, the General Practitioner Assessment of Cognition, and the Hopkins Verbal Learning Test.

Delivering a full cognitive assessment usually consists of multiple sets of interactions between the test subject and the test deliverer where, on the basis of performance so far, additional instructions or prompts are delivered and further tasks or puzzles given until a given performance criterion is reached. Computerised cognitive testing systems such as the Cambridge Neuropsychological Test Automated Battery (CANTAB) automate all aspects of the cognitive testing procedure including the ordering of tasks, all aspects of task presentation, interactive instructions and scoring of the tasks.

Nevertheless, cognitive and physiological state cannot be perfectly predicted by cognitive scores and/or clinical or demographic information due to several limitations of the current state of the art. Cognitive state is defined as the subject's ability to perform specific cognitive functions of the brain, such as memory, attention, executive function, language. Physiological state is defined as subject's experiences of pain, fatigue, sedation, and alertness.

One limitation of cognitive tests is a need to remain user-friendly/tolerable in order to ensure compliance while pushing the upper limits of performance. Without testing beyond the limit at which the user can easily respond, cognitive tests have no way of measuring the upper boundary of a person's cognitive capability. This experience can be frustrating to users and can make tests time-intensive which is logistically problematic and expensive in clinical trials and clinical practice.

Another limitation is that for some cognitive tests, the same performance can be achieved by using different strategies, which employ different brain circuits or functions. For example, on a test of memory, two people can use different strategies to produce the same score: one using a learnt strategy such as a mnemonic, and another without a strategy. Although both persons may achieve the same score, the loading of neural circuits relating to memory would be expected to be higher in the second person. Alternatively, the two persons may produce different scores for the same level of memory ability because of the difference in strategy use.

Other limitations include subjective experience and cultural variation, such as 'faking' poor performance and differences in motivation leading to differences in performance. For example, a patient experiencing mild levels of pain may exaggerate pain reports on purpose to receive opioid drugs. Therefore, there is a need in the art for a user-friendly system that allows accurate measurement of a person's cognitive abilities and physiological state using objective markers in the response stream.

One objective way of measuring physiological state is extracting features from the voice and speech. The human voice contains important information about our neural processing through what we say and how we say it. In adult humans, we express and assess subjective physiological states such as pain, sedation, fatigue and mood through both content of speech and other features of speech, including the rate of word production, fluency of speech and tone of voice. In pre-verbal children and in animals, these states can be inferred from non-word vocalisations.

Previous research (Lautenbacher et al., 2017) found changes in acoustic features of vowel production to significantly predict changes in subjective pain perception. Fifty healthy young adults produced the vowels 'u', 'a', 'i', and 'schwa' (a in 'alone' and u in 'circus') while immersing their hands into hot water and under baseline (no heat immersion). The phonetic parameters extracted were pitch (mean f0), f0 range, and loudness. Pitch and loudness of the vowels 'u' and 'schwa' were found to increase during pain, and a greater increase in these phonetic parameters was associated with a greater increase in subjective pain scale ratings.

Another study (Oshrat 2014) has demonstrated that, in principle, machine-learning based classification algorithms can differentiate between speech samples taken from people with or without significant pain. In a small Israeli study, 97 recordings taken from a total of 27 adults with traumatic injuries that gave pain were used to generate between 3 and 6 one-second voice clips from each recording, in which either digits from their ID number or words from their name were spoken. Using machine learning, the authors were able to select a set of features that correctly classified pain/no pain classifications in around 80% of male samples and 83% of females.

Whereas Oshrat and colleagues (2014) were unable to use the method to develop a marker of pain that replicated the multiple levels of a clinical scale (e.g. a 1-10 scale, as opposed to a binary pain/no pain criterion) due to the small sample size, Tsai et al (2016) were able to classify pain intensity in both binary (pain/no pain) and ternary (mild/moderate/severe pain) classes, with 72.3% and 51.6% accuracy respectively. This study employed a support vector machine that used both acoustic characteristics extracted from speech recordings as well as facial features extracted from video recordings.

Together, these studies provide proof of the principle that machine-learning based analysis of very brief speech samples can discriminate voice features that relate to pain.

Similarly, artificial intelligence (AI) based models have been used to infer physiological state from voice alone as well as in conjunction with other variables (e.g. video recordings, demographic variables, disease specific variables, and cognitive performance) in other areas of neurology and psychiatry, including depression (Williamson et al., 2014), frontal lobe dementia (Nevler et al., 2017), Autism spectrum disorder (Fusaroli et al., 2017), Parkinson's Disease (Zhang et al., 2016), and post-traumatic stress disorder and depression (Place et al., 2017).

It is therefore known in the art that certain physiological states can potentially be inferred from speech. One of the problems to be overcome in the use of speech as a marker of physiological state is the inherent variability in human speech.

Variation in speech signal in humans can be produced by a number of factors:
  A) Variation between speakers due to biological variation such as sex, age, characteristics relating to the size and shape of the voice anatomy, voice disorders, smoking
  B) Variation due to learnt behaviours (educational level, language, regional accent, speaking style)
  C) Sound recordings of voices may also reflect variation in the recording environment (background noise, quality of data recording and microphone)
  D) Variation within speakers when tested on different occasions due to factors other than cognitive or physiological state e.g. hydration, humidity, vocal loading There are also two sources of variation that relate to the psychological context of the task:
  E) Variation within speakers when tested on different occasions due to current cognitive or physiological states e.g. delirium, dementia, depression, anxiety, pain, fatigue (e.g. Johnstone 2001 UWA; Vogel et al., 2010)
  F) Variation within speakers when tested on the same occasion but under different task conditions e.g. high versus low cognitive load; multitasking (e.g. counting while simultaneously controlling body posture (Andersson et al., 2002), stress related to the simultaneous presence of multiple stressors, such as environmental noise plus cognitive load (Marquard et al., 2017), high versus low emotional load (Johnstone 2001, UWA).

These sources of variation are particularly challenging in patients with psychiatric and neurological conditions.

Many brain conditions cause changes to voice and speech (A). Dysarthria is the medical term for difficulty speaking, caused by developmental or acquired brain disorder or by medication. It can include a range of symptoms such as slurred, nasal-sounding or breathy speech, a strained and hoarse voice, excessively loud or quiet speech, problems speaking in a regular rhythm, with frequent hesitations, "gurgly"-sounding or monotone speech and difficulty with tongue and lip movements Patients with temporary (e.g. drug-induced) or permanent (e.g. neurodegeneration) brain changes are more likely to have a lower tolerance of cognitive or emotional load, or other stressor, and a reduced ability to multitask (F).

Patients with brain disorders are also more likely to suffer comorbid symptoms such as depression, pain, or fatigue (E).

An improved system for monitoring the brain function through voice samples should take into account, limit or control the inherent variability in the individual voice characteristic of each person.

The present invention aims to at least partially address some of the problems above.

A first aspect of the present invention provides a system for assessing the physiological state of a subject, comprising: a task delivery module configured to communicate to a subject at least two sets of information, each set of information relating to a cognitive task requiring a spoken response from the subject; a response detection module configured to record the respective spoken responses from the subject as an audio signal, the response detection module comprising a microphone; an analysis module configured to analyse the audio signals corresponding to the respective spoken responses recorded by the response detection module to determine from the respective spoken responses one or more characteristics indicative of the physiological state of the subject, compare said characteristics from the respective spoken responses, and determine the physiological state of the subject based on said comparison.

Optionally, the communicated sets of information are selected from different groups of pre-stored sets of information, said pre-stored sets of information being grouped according to a cognitive load associated with the task to which each set of information relates. Alternatively, or additionally, the communicated sets of information are selected from different groups of pre-stored sets of information, said pre-stored sets of information being grouped according to a physical or mental state induced by the task to which each set of information relates.

Brain function can be inferred from speech but variation amongst individuals can pose a challenge. Further variations occur between speech samples obtained from the same individual at different time points based on the individual context at the time the samples are obtained. Speaking under conditions which require additional brain processing (e.g. while engaging in physical activity or complex behaviours like driving) or stressors (e.g. public speaking, when tired, stressed, in pain etc.) also leave a signal in the voice. These signals are likely distinctive between states because individual cognitive functions are differentially affected by various states.

The invention addresses problems in the art by comparing an individual's voice features under two conditions on the same occasion to cancel out feature variation that is due to differences between individuals (A & B above) and due to aspects of the testing occasions or environment that are not related to mental or physiological state (C & D above). This leaves voice feature variation due to task conditions (F) and current physiological state (E). In addition, by actively engaging individuals in cognitive challenging tasks, and moderating level of difficulty of the task based on performance, the invention minimises 'faking' of performance and symptoms of disease, thus maximising unmasking of 'true' cognitive ability and physiological state. Task conditions (F)

and current physiological state (E) exacerbate some aspects of the voice signal and minimise others.

Therefore, in one embodiment of the invention, the task conditions (F) will be systematically varied, for example by increasing and decreasing the cognitive load required to complete the task at hand. This will produce performance and voice signals related to each cognitive load. The difference in task performance and the voice characteristics recorded during performance between cognitive loads on the same task can be represented as delta scores for each individual participant. This delta alone can be used as a generic marker of brain effort within each individual person. Furthermore, the delta score can then be compared to the delta obtained under high vs low load conditions in patients with known physiological states in a training set, and a probability of that state produced by an AI model. Therefore, this signal can be added to cognitive performance scores and other known predictors of physiological state (e.g. clinical scores, demographics) to improve a predictive model of physiological state and neurological or neuropsychiatric disorder.

A second aspect of the invention provides a method of assessing the physiological state of a subject, comprising: communicating to a subject at least two sets of information, each set of information relating to a task requiring a spoken response from the subject; recording the respective spoken responses from the subject as an audio signal using a microphone; analysing the audio signals corresponding to the respective recorded spoken responses to determine from the respective spoken responses one or more characteristics indicative of the physiological state of the subject, comparing said characteristics from the respective spoken responses, and determining the physiological state of the subject based on said comparison.

A third aspect of the invention provides a mobile computer device for use in the method of the second aspect comprising: one or more processors; a user interface controlled by the one or more processors and configured to communicate to a subject at least two sets of information, each set of information relating to a cognitive task requiring a spoken response from the subject; a microphone controlled by the one or more processors configured to record the respective spoken responses from the subject as an audio signal; a memory operatively coupled to the one or more processors configured to store the respective audio signals; a communication device configured to communicate the respective audio signals to a remote server; a communication device configured to communicate the respective audio signals to a remote computer, said remote computer configured to analyse the audio signals corresponding to the respective spoken responses recorded by the response detection module to determine from the respective spoken responses one or more characteristics indicative of the physiological state of the subject, compare said characteristics from the respective spoken responses, and determine the physiological state of the subject based on said comparison and communicate the results of said determination to the mobile computer device; wherein the user interface is configured to communicate information based on the results of the determination received from the remote computer to the mobile computer device.

Figure 2:
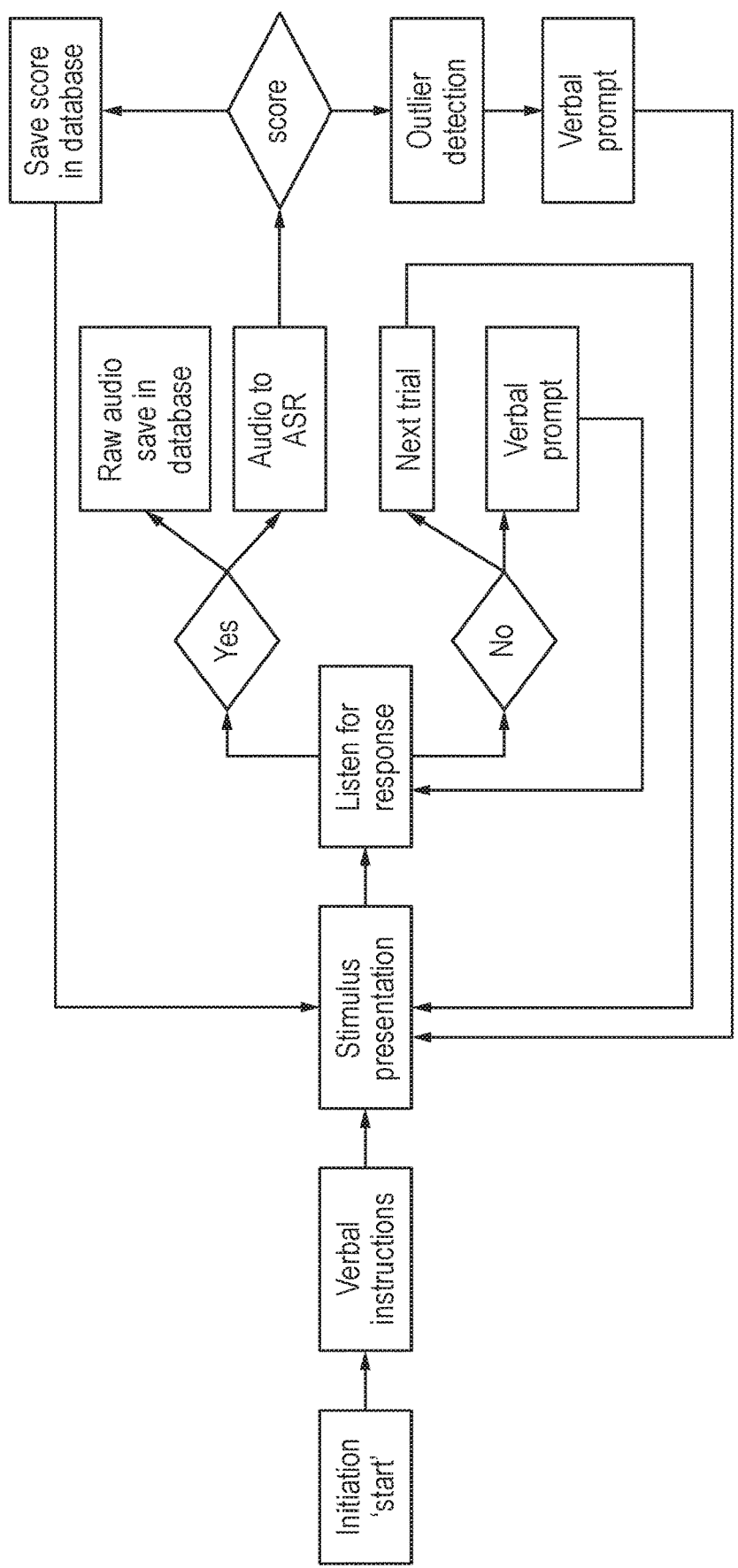
Figure 3:
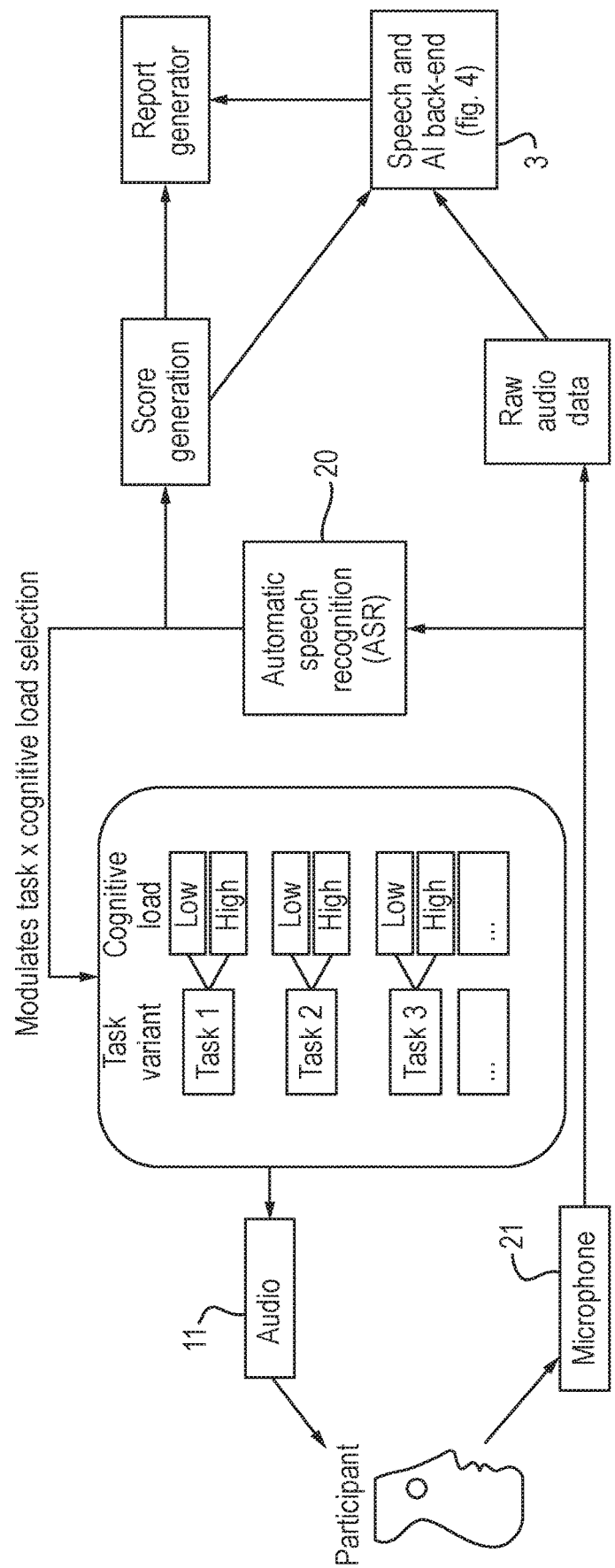
Figure 4:
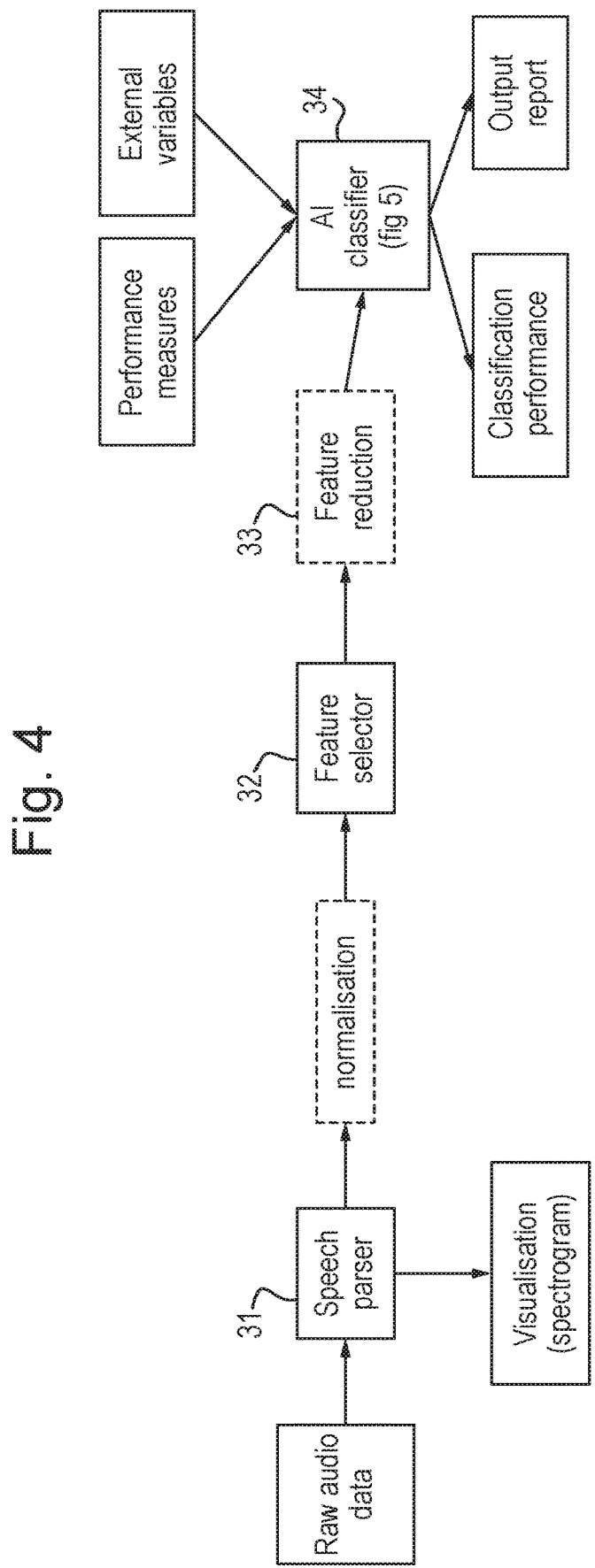
Figure 5:
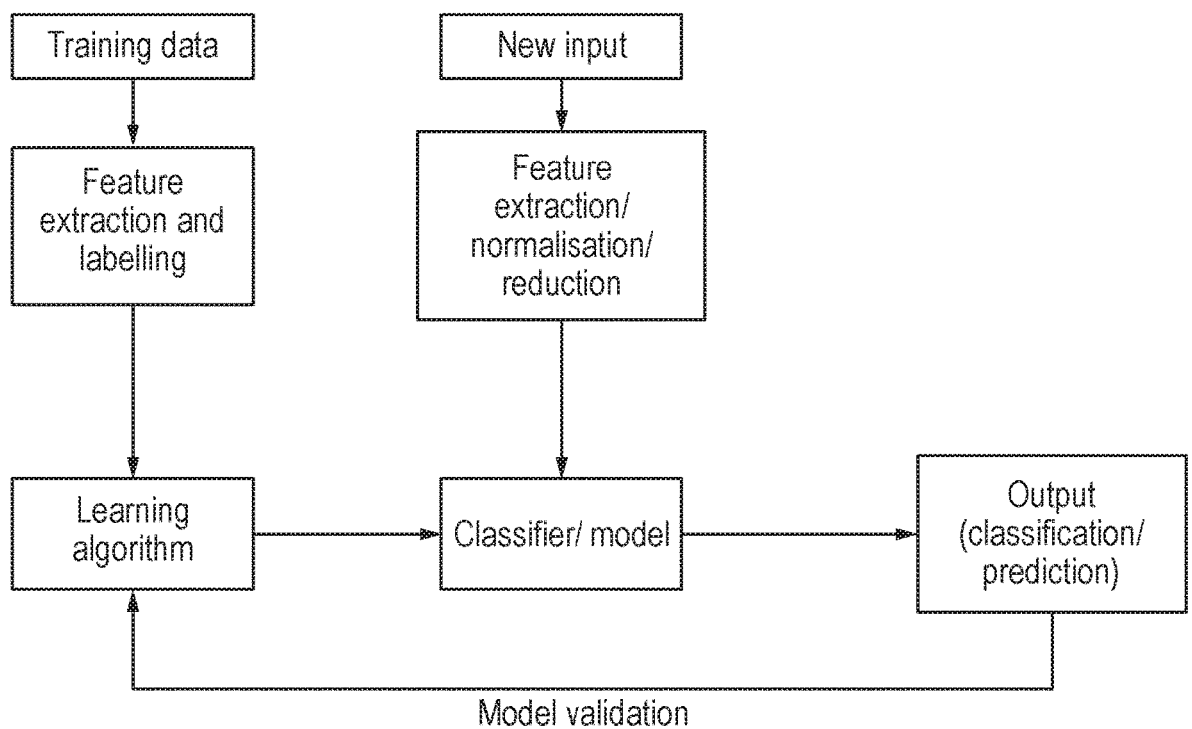

A fourth aspect of the invention provides a computer device for use in the method of the second aspect, comprising: one or more processors; a communication device configured to receive at least two audio signals from a mobile computer device, said audio signals corresponding to recorded responses to respective cognitive tasks performed by a subject; wherein the one or more processors are configured to analyse the audio signals corresponding to the respective spoken responses to determine from the respective spoken responses one or more characteristics indicative of the physiological state of the subject, compare said characteristics from the respective spoken responses, and determine the physiological state of the subject based on said comparison and communicate the results of said determination to the mobile computer device. The invention will be described in further detail below by way of non-limiting examples, with reference to the accompanying drawings in which:

FIG. 1 shows an example system of the invention;
FIG. 2 shows an example of part of a front-end system;
FIG. 3 shows an example of part of a front-end system;
FIG. 4 shows an example back-end system;
FIG. 5 shows an example of AI system training.

FIG. 1 shows an embodiment of a system for assessing the physiological state of a subject. The system comprises a task delivery module 1 configured to communicate to a subject at least two sets of information, each set of information relating to a cognitive task requiring a spoken response from the subject, and a response detection module 2 configured to record the respective spoken responses from the subject as an audio signal, the response detection module 2 comprising a microphone 21. The task delivery module 1 and the response detection module 2 together form a 'front-end' of the system. The front-end (response detection module 2) may pass the recorded audio data to a 'back-end' analysis module 3. The analysis module 3 may receive real-time voice signal data during a task.

In the embodiment shown in FIG. 1, the system of the invention may be provided by a computer, phone, wearable, or other electronic device (i.e. a mobile computer device). The device may interactively deliver cognitive or clinical task instructions (verbally through a speaker 11 and/or through other means e.g. visually on a screen) and records subject responses (verbal via a microphone 21 and optionally also visual, gesture or manual responses via a camera or manual user interface). From these responses, cognitive and clinical scores are calculated.

In another embodiment, the system may be provided by a mobile computer device and a remote computer (e.g. a server). The mobile computer device may include the task delivery module 1 and the response detection module 2. The remote computer device may include the analysis module 3. Data is communicated between the mobile computer and the remote computer.

The task delivery module 1 may be configured to deliver a battery of cognitive tasks. Each task will include instructions (e.g. verbal), lists of words, numbers, associations, sounds, questions, and other information, as well as sequences of prompts, designed to cue a verbal response from the user. The response detection module 2 is configured to perform response handling functions and may use Automatic Speech Recognition (ASR) and Natural Language Understanding (NLU) systems to interpret semantic aspects of the voice response.

The cognitive tasks may include parameters that can be manipulated to increase the difficulty (i.e. increase in cognitive load) of the task with respect to different aspects of cognition. For example, a task designed to measure working memory may be parameterised so that the number of items to be recalled increases, or the complexity of the manipulation of the recall items demanded increases, or the degree of similarity between items is reduced.

Accordingly, the communicated sets of information may be selected from different groups of pre-stored sets of information, said pre-stored sets of information being grouped according to a cognitive load associated with the task to which each set of information relates. Information pertaining to tasks of different difficulties may be pre-stored, e.g. in a memory associated with the task delivery module 1.

Tasks delivered by the task delivery module 1 may not necessarily differ in the cognitive load (e.g. those explicitly mentioned above) but may alternatively or additionally differ in the mental or physiological state induced by the task. For example, the subject may be instructed to recite a list of four numbers while listening to a first piece of music (first task) and then recite a list of another four numbers while listening to a second piece of music (second task). Although, the recitals may be considered to have the same associated cognitive load, the different conditions (i.e. music) may induce different mental and physiological states in the subject, which may affect the performance of the recitals.

Examples of conditions which may induce a particular physical or mental state include: viewing of different images, listening to different sounds or music, performing different physical activities, recalling emotional memories, ingesting medication or nutritional supplements, focusing attention on pre-existing disease or symptoms, inducing mental imagery, verbal priming, manipulating performance feedback to user. Some conditions (e.g. images, sounds, music, mental imagery, memories, verbal priming, feedback manipulation) may induce a particular mental state, for example if the conditions are selected to be particularly distressing, calming, pleasant or unpleasant, for example. Some conditions may (e.g. physical activities, medication, supplements) may induce a particular physical or mental state if the conditions are selected to induce fatigue, sedation, mental alertness or cause pain to the subject, for example.

Accordingly, the communicated sets of information may alternatively, or additionally, be selected from different groups of pre-stored sets of information, said pre-stored sets of information being grouped according to a physical or mental state induced by the task to which each set of information relates. The tasks may have the same or different associated cognitive loads. Information pertaining to tasks of different difficulties may be pre-stored, e.g. in a memory associated with the task delivery module 1.

The task delivery module 1 may also include internal logic that adaptively modifies the flow and difficulty of the tasks in response to both the semantic content of the subject's responses and optionally, to real-time input from the voice analysis engine. The internal task logic may continually adapt the difficulty of the trials during the task flow until the subject makes a certain number of errors, or until the system detects a target change in the voice signal, such as a required stress level indicator. The task delivery module 1 may also include internal logic configured to use semantic performance and or voice feature information from a prior task to adapt the flow and parameters of a subsequent task.

Accordingly, the response detection module 2 may comprise a speech recognition module 20 configured to analyse each spoken response, the response detection module 2 may be configured to compare the output from the speech detection module with a pre-stored expected response, and allocate a score to each spoken response based on said comparison. The task delivery module 1 may be configured to select a set of information relating to a next task based on the score associated with a response to a previous task. If the score for the previous task is lower than a predetermined threshold score, the next task may be selected so as to have an associated cognitive load lower than the cognitive load associated with the previous task. If the score for the previous task is higher than a predetermined threshold score, the next task may be selected so as to have an associated cognitive load higher than the cognitive load associated with the previous task. If the score for the previous task is determined to be an outlier, the next task may be selected so as to have an associated cognitive load the same as or similar to the cognitive load associated with the previous task.

Alternatively, or additionally, the system may determine the cognitive load of a task based on the response detected by the response detection module 2. For example, the analysis module 3 may determine the cognitive load of a task based on characteristics of the spoken response. The characteristics may include the same characteristics as those used to determine the physiological state of the subject, e.g. pitch, intensity, formant frequencies, glottal flow, speech duration, speech rate, and voice quality. However, these may be parameterised differently in each case.

In a study directed to this feature, sixty participants aged 21 to 78 completed an automated verbal test of working memory. Working memory span ranged from 3 to 8 items. Responses were categorised as "high load" if they were >0.6 of that participant's maximum span. Audio features extracted from each response were normalised for each participant, expressing within-subjects differences in vocal features across trials of varying load. Data were divided into training (70%) and test (30%) datasets, and analysed using a Support-Vector Classifier (SVC) predicting cognitive load condition. Classification accuracy on the test data was 88% in distinguishing high and low cognitive load on the basis of vocal features alone, from recordings taken in variable environments, recording conditions and background noise.

The system may optionally provide feedback to the subject, e.g. as voice response such as 'correct', 'incorrect' or audio tones. The internal logic of the task delivery module 1 may manipulate the feedback (by providing false positive or negative feedback) in order to induce changes in the user's current mental state, and thus elicit changes in voice signal.

Accordingly, the information response detection module 2 may be configured to communicate to the subject information based on said score for a present task, before communicating a set of information relating to a next task.

FIG. 2 shows an example of a front-end system in which the response detection module 2 listens for a response. If no response is detected, a verbal prompt and/or another task may be communicated. If a response is detected, the audio data is stored in a memory and passed to the speech recognition module 20 to be scored and simultaneously passed to the back-end AI module. The score is then stored, associated with the response. If the score is determined to be an outlier (e.g. if a response is detected but it does not pertain to the task) a verbal prompt may be communicated for the user to respond again.

FIG. 3 shows an example of a front-end system in which the cognitive load of tasks communicated by the task delivery module 1 are modulated based on the output of the speech recognition module 20.

The following examples of cognitive tasks may be used in the present invention. However, this is not an exhaustive list. Some types of task will be designed with trials that vary in cognitive load in a stepwise/parametric fashion, allowing for comparisons between conditions (i.e. delta score), in terms of cognitive performance and the associated voice features.

Other tests are designed specifically to maximise or optimise voice feature extraction under different mental and physical states induced by tasks.

1) Verbal Digit Span—Forwards

Participant is instructed to listen to and then repeat back a sequence of digits. Cognitive load is varied between conditions by manipulating the number of digits within the sequence of each trial. For example, trial 1 (low cognitive load) will present a short sequence of digits (e.g. "7 . . . 1 . . . 3 . . . 4"), whereas trial 2 (high cognitive load) will present a long sequence of digits (e.g. "9 . . . 6 . . . 5 . . . 8 . . . 7 . . . 1 . . . 3 . . . 4"). Both conditions require holding a sequence of digits in short term memory. However the contrast between the two conditions is in the short term auditory memory load.

2) Verbal Digit Span—Backwards

Similar to the forward verbal digit span task, where the participant is instructed to listen to a sequence of digits. However, in this task, the participant is instructed to repeat the digits back in reverse order. For example, when the participant hears "4 . . . 3 . . . 1 . . . 7", the correct response is "7314". Cognitive load can again be increased by increasing the number of digits in a sequence.

In addition to short term auditory memory engagement, the backward digit span requires that the digits be manipulated using working memory. Therefore, comparing forward with backward digit span performance will derive a measure for working memory load.

3) Verbal Paired Associates Learning (Verbal PAL)

Participant is instructed to listen to pairs of words and then prompted with one of the pair, and asked to respond with the second word. Cognitive load is manipulated by the level of semantic similarity between the pairs. An example for low cognitive load (high semantic similarity) may be "grass—green", whereas an example for high cognitive load (low semantic similarity) may be "grass—loud". The contract between cognitive load trials reflect associative learning ability.

4) Non-Word Verbal Paired Associates Learning (Non-Word PAL)

This task is a variation of the verbal PAL, where words are paired with non-words. These are words that can be pronounced as a real world, but that do not have a semantic association/meaning, for example "narav". This task is more challenging than the verbal PAL as participants will not be able to rely on semantic strategies to learn pairs, thus demanding stronger associative learning ability.

5) Verbal List Learning

In this task, participants are instructed to listen to a list of words and to recall as many items on the list as possible. Measures of interest in this task are number of correct response, which reflect memory performance, as well as voice features such as pauses, breathing, stuttering, fillers ('ehm', 'err', 'pff').

6) Sentence Repetition

Participants are instructed to listen to a sentence and asked to repeat this sentence back in the exact same words. Cognitive load can be manipulated by increasing the number of words within each sentence and/or varying the syntactic complexity of the sentence structure. For example, "the cat sits on the table" is less challenging to process and remember (low cognitive load) than "the ball in front of the pen than is broken is rolling away" (high cognitive load).

7) Verbal Fluency—Semantic Categories

Participants are instructed to name as many words as they can that fit into a semantic category. For example, a category can be 'animals', and responses can include 'cat, dog, frog, elephant, rhinoceros, bird' and more. Measures of interest in this task are total number of responses and number of correct responses which reflect verbal fluency, as well as voice features such as pauses, breathing, stuttering, fillers.

8) Verbal Fluency—Phonological

A variation of the semantic verbal fluency task, this task instructs the participant to name as many words that start with a particular letter or sound. For example, words that start with the letter 't' include 'task, test, timid, thin, tree, tame'. Words that start with the sound '/f/' include 'fish, phone, fire, fist, pharaoh' and more. Measures of interest in this task are total number of responses and number of correct responses which reflect verbal fluency, as well as voice features such as pauses, breathing, stuttering, fillers.

9) Similarities

Participants are presented with a pair of words and asked to explain how the pair of words are alike or similar. Cognitive load can be varied by manipulating the abstraction of the relationship between words. For example, "how are 'green' and 'blue' alike?" may prompt the response "they are both colours" (low cognitive load). In contrast, "how are 'war' and 'peace' alike?" requires an answer such as "they can political states of a country" (high cognitive load). Note that "they are opposites" is not a correct answer to this trial as they question asks for how two words are similar, not different. Contract between conditions reflect verbal reasoning ability.

10) Verbal Emotion Recognition

In this task, participants are presented with short audio clips (e.g. tones, music, speech) that have an emotional label (potentially acquired via crowd-sourcing during development of task). They are asked to select the emotional category that they think correspond to the stimulus presented (e.g. happy, sad, anger, surprise, fear, disgust). Measures of interest in this task include number of correct responses, as well as bias in neutral emotion classification.

11) Sustained Phonation

Participants are instructed to produce a stable sound for a fixed duration of time. For example, saying 'aaaa' for 2 seconds. The ability to produce and sustain a continuous sound allows for characterisation of voice quality features such as jitter and shimmer. Voice features extracted from this task is expected to change under different mental and physical conditions (e.g. fatigue, stress, pain, sedation, happy, sad).

12) Diadochokinesis Task (Pa-Ta-Ka)

In this task, participants are instructed to repeat a syllable or a combination of syllables quickly for a fixed duration of time, for example repeating syllable 'papapa' quickly for 2 seconds (low cognitive load) or repeating 'pataka' quickly for 2 seconds (high cognitive load). This task assesses oral motor skills and is sensitive to speech disorders such as dysarthria.

13) Paced Auditory Serial Addition Task (PASAT)

Single digits are presented every 3 seconds and the participant is instructed to add each new digit to the one immediately prior to it. Cognitive load can be manipulated by varying the time interval between digits (inter-stimulus interval—ISI). For example, shorter ISI increase task difficulty, thus higher cognitive load. Contracts between conditions reflect sustained attention, auditory information processing speed and flexibility.

14) Serial Subtraction

Participants are instructed to count down from 100 by subtracting a particular number. Cognitive load can be manipulated by varying this particular number to be subtracted. For example, counting down from 100 in steps of 1 or 2 (low cognitive load) is easier than counting down from 100 in steps of 7 or 9 (high cognitive load).

15) Familiar Sequences

This task instructs participants to recall familiar sequences from memory quickly. For example, 'name the days of the week as quickly as you can, starting from Monday', 'count from 1 to 20 as quickly as you can'. Cognitive load can be manipulated by instructing participants to recall familiar sequence in reverse order, for example 'count backwards from 20 to 1 as quickly as you can', 'name the days of the week backwards, starting from Sunday, as quickly as you can'. Contracts between conditions will reflect difficulty in processing speed and working memory ability.

16) Verbal Questionnaire Administration

Standardised questionnaires will be adapted for use on the voice platform in this invention. Most existing questionnaires in the art rely on participants manually completing open-ended questions and rating scales (either using computer button responses or pen and paper). This method requires time, is found boring by users, and is not always appropriate, for example for use with visually impaired patients or people with a learning disability. This invention aims to improve on the existing art by adapting such questionnaires into an audio platform using conversational methods and AI to improve the user experience, while maintaining clinical validity and reliability. Open-ended questions from standardised questionnaires will also illicit rich audio data from which voice features will be extracted.

Accordingly, the cognitive tasks delivered by the task delivery module 1 may include: a forward verbal digit span, a backward verbal digit span, verbal paired associates learning, non-word verbal paired associates learning, verbal list learning, sentence repetition, semantic category verbal fluency, phonological verbal fluency, similarity recognition, verbal emotion recognition, sustained phonation, diadochokinesis, paced auditory serial addition, serial subtraction, familiar sequences, and a verbal questionnaire.

The analysis module 3 is configured to analyse the audio signals corresponding to the respective spoken responses recorded by the response detection module 2 to determine from the respective spoken responses one or more characteristics indicative of the physiological state of the subject, compare said characteristics from the respective spoken responses, and determine the physiological state of the subject based on said comparison. Optionally, the analysis module 3 may be configured to determine the physiological state of the subject based additionally on the score determined by the response detection module 2.

The analysis module 3 may extract relevant signals of a subject's cognitive and emotional state and changes in said state. These signals may be time-indexed in order to be able to map the state signal to the task-flow, and therefore infer the causal link between task and physiological state. Alternatively, the signal may be an aggregate feature of the subject's entire audio response.

Audio data corresponding to responses may be analysed with respect to three general types of features: 1) paralinguistic features, 2) prosodic features related to pitch, 3) voice quality features. Established methods in the art may be used to extract these signals, such as mel-frequency cepstral coefficients (MFCC) analysis, Perceptual Linear Prediction (PLP), and Linear Predictive Coding (LPC) (Huang, Acero, and Hon, 2001). More specifically, the following features, as well as others available in open-source software like openSMILE, will be extracted, normalised, and used by the analysis module 3:

Pitch is the psychological perception of changes in frequency. For example, increase in frequency is perceived as rise in pitch. The pitch of a complex tone (speech) corresponds to the fundamental frequency (f0). Pitch also reflects the frequency of vibrations of the vocal chords during speech production. For example, a question has a rising pitch, whereas a statement or declaration has falling pitch. Various statistics of pitch, which correspond to different features of the speech signal, will also be measured:

fundamental frequency (f0)

f0 mean, SD, range, median f0 slope (e.g. rising, falling, flat)

Intensity is the sound pressure, and is a physical property of the acoustic signal. It is the measure of energy carried by a sound, that leads to the perception loudness. Statistics related to intensity that will be extracted include:

mean, SD slope curvature

Formant frequencies are determined through the measurement of the Linear Predictive Coding (LPC). These characterise the shape of the vocal tract, which in turn is determined by the position of the articulators (tongue, lips, jaw, velum/soft palate).

Glottal flow is the volume velocity flowing through the glottis and as such, is the excitation source of voiced speech. Glottal flow can be combined with a lip radiation model (high-pass filter in frequency domain) to form the glottal flow derivative. Changes in voice quality are reflected in the glottal flow.

Speech duration is measured as length in seconds. This can be applied to full utterances, sentences, words, or syllables (often distinguished between stressed and unstressed syllables).

Speech rate:
  words per second
  syllables per second
  number of pauses
  length of pauses
Voice quality covers a wide variety of features that are attributed to imperfect control of the vocal fold vibrations that produce speech. The perceived effect results in hoarseness, breathiness, creakiness etc.:
  jitter (irregularities in pitch)
  shimmer (irregularities in intensity)
  harmonic-to-noise ratio (HNR)
  cepstral analyses (frequency of change in frequency signal)

Accordingly, the characteristics indicative of physiological state determined by the analysis module 3 may include: pitch, intensity, formant frequencies, glottal flow, speech duration, speech rate, and voice quality. A value may be determined which is associated with one or more of these characteristics. The analysis module 3 may be configured to compare said characteristics (e.g. values thereof) and determine a change in any one of said characteristics between the spoken responses.

As shown in FIG. 4, the audio data may be fed into a speech parser module 31. This module incorporates an algorithm to detect portions with certain durations or features within the full audio (e.g. full utterance, sentence, words, syllables) and either label these or segment these. In addition, speech signals will be labelled with meta-data that indicate cognitive load and mental or physical state.

Accordingly, the analysis module 3 may comprise a speech parser module 31 configured to detect portions of a response corresponding to speech features and label and/or segment the detected portions, said speech features including full utterances, sentences, words and syllables.

As shown in FIG. 4, the speech parser module 31 may then feed these segments into a feature selector 32, which extracts acoustic features. These features are extracted and analysed on a frame-by-frame basis as well as at the full utterance level. Therefore, both local (frame-by-frame or other defined subsample of full audio) and global (derived over total utterance) features will be derived. Analyses of these features include calculating delta values for features derived from high compared to low cognitive load trials.

Optionally, as shown in FIG. 4, the features extracted by the feature selector 32 may pass through a feature reduction module 33. Depending on the nature of the cognitive task performed, and the manner of voice feature extraction, certain combinations of features may provide more accurate results than others. For example, a memory task that requires a person to recall a list of numbers in turn will produce discrete short utterances, whereas a free speech task produces a long continuous speech stream. The features of interest in the first task may relate to the low-level acoustic properties of each discrete word uttered, whereas the features of interest in the second task may include paralinguistic features such as speech rate, number of pauses, breathing, stuttering etc. Moreover, a frame-by-frame analysis of the speech signal will be less informative in the first task compared to the second. Therefore, rather than classify the speech on the basis of all of the derived features, it may be desirable to utilise a subset of features. Reducing the total number of features to be fed into the AI back-end may also increase the speed of the classification and prediction process.

Accordingly, the analysis module 3 may be configured to determine the characteristics indicative of physiological state from a subset of the speech features detected by the speech parser module 31, said subset of features being selected based on the tasks to which the communicated information relates. Alternatively or additionally, the analysis module 3 may be configured to determine the physiological state of the subject based on a subset of the one or more characteristics, said subset being selected based on the tasks to which the communicated information relates. Alternatively, the analysis module 3 may be configured to determine the physiological state of the subject based on the full raw audio data of the subject response.

It should be noted that although the speech parser, feature selector and optional feature reduction process are described as separate elements, in practice, these elements may be implemented and executed by the same physical system (e.g. server, cloud).

The analysis module 3 may then combine cognitive and/or clinical scores output by the system, demographic features and any other externally-known information (e.g. diagnosis, biometric data, brain imaging data), technical input features of the devices used to record, and the raw audio signal or the feature selector output (i.e. analysed audio features). This can happen in real time or later; in the device or the cloud.

Depending on the types of features extracted as well as the number of features extracted and retained, an AI classifier 34 may be used. Different AI classifiers 34 may be used, for example, a Gaussian classifier, a nearest-neighbour classifier, a neural network or sparse partial least square model may be used for different sets of features. Alternatively, if a particular AI model is preferred, this can guide the feature selector and feature reduction processes.

The output of the algorithm is then optionally compared against norms or prior scores.

Accordingly, the analysis module 3 is configured to determine the physiological state of the subject based additionally on stored prior scores. Alternatively or additionally, the determined physiological state of the subject may be compared to a predetermined baseline.

The analysis module 3 may optionally output its determination as a report. The output of the invention may report any or all of the following:

Participant's physiological state at that particular point in time. For example, in the case of chronic pain, whether the participant is in mild, moderate or severe pain.

Participant's risk for disease, when the analysis module 3 compares scores and features against norms.

Change in physiological state or disease (i.e. disease progress), when the analysis module 3 compares scores and features to prior scores and features of same participant.

Effect of a drug/device/intervention, when the analysis module 3 compares scores and features across external known conditions.

The audio data may be pre-processed using normalisation methods to exclude variations related to age, gender and to extract low-level features such as energy, intensity, pitch, formants, glottal flow, speech duration and rate, voice quality and spectral shape descriptors. Standard supervised machine learning techniques may be used to train the system to recognise the target cognitive or emotional state from the low-level features. An example system that uses this approach is the openSMILE Audio Feature Extractor (the Munich open Speech and Music Interpretation by Large Space Extraction toolkit) (Eyben et al. 2013).

Alternatively, the raw audio data from each subject response may be fed into a deep learning system without pre-processing. An example system that uses this approach is Deep Mind's WaveNet, a deep generative model of raw audio waveforms. Deep learning typically provides computational models that are composed of multiple processing layers to learn representations of data with multiple levels of abstraction. Deep learning typically determines intricate structure in large data sets (including audio data) by using backpropagation algorithms to indicate how a machine should change its internal parameters that are used to compute the representation of the data in each layer from the representation in the previous layer.

Alternatively, raw audio data may be fed into a neural network. One example of this approach is to use raw magnitude spectrogram features fed into a deep convolution neural network. Another approach is to feed the raw audio waveform in to a deep network, in which case a feature extraction step may not be required.

Regardless of the machine learning approach used, the method used to obtain the training data is important. The training data may comprise of a set of audio samples and corresponding physiological state labels.

In one example, the training data may be obtained by testing participants using a special variant of the front-end system that has been configured to optimise the quality of the training data. Optimisations may include increasing the length of the testing session, the dynamic range of the task parameters, manipulation of the feedback provided to subjects, and specific selection of the testing battery optimised for a subsample of the population characterised by age, gender, education, occupation, physiological and/or disease state.

The physiological state labels may be obtained through a combination of any or all of the following:
  Induction of physiological state via front-end task difficulty titration
  Induction of physiological state via external means such as causing pain, increasing distractors (e.g. noise), conducting dual-task to increase cognitive load (e.g. postural/balance task), and manipulating feedback presented to participant
  Imputation of physiological state from participant task performance
  Estimation of physiological state via physiological measures such as facial emotion recognition, skin conductance and heart rate known to be proxies for stress
  Measurement of physiological state via brain imaging data (e.g. EEG, MRI) of brain circuit activation
  Determination of physiological state based on patient self-report
  Determination of physiological state based on clinician assessment or diagnosis
  Determination of physiological state based on medical records, standardised questionnaires and patient self-report In another example, the training data may be obtained by data-mining existing speech corpora of healthy individuals performing cognitive tasks of varying cognitive load, as well as speech corpora of speech samples from patients with known medical conditions. These speech samples of patients may be found within the public domain (such as YouTube®) or acquired via collaborations with academic institutions and not-for-profit organisations such as Research and or Patient Support Charities. Physiological state labels in these data sets may be obtained through a combination of any or all of:
  Computation of delta features within each individual
  Known labels determined during data collection by owners of the databases
  Labelling of data samples via a crowd-sourcing platform As illustrated in FIG. 5, to train a back-end AI system, the AI system receives input from external resources, i.e. data not generated by the front-end module. Examples of such external data include, but is not limited to, speech samples from existing speech corpora of healthy individuals performing cognitive tasks of varying cognitive load, or speech corpora of speech samples from patients with known medical conditions.

The training datasets will have been labelled in accordance with predefined classes of interest. For example, in the case of chronic pain, these labels may be 'mild', 'moderate', and 'high'. They may also have additional labels characterising cognitive or emotional load, e.g. 'low' or 'high'.

Depending on the type of training datasets, either or both of the following training methods may be used to fine-tune the AI classification system.

In one example, when the dataset comprises several data points within the same individuals (within-subject repeated measures paradigm), a digital platform (computer, cloud, server) receives audio samples and speech signal processing occurs, which include extraction of audio signals under different conditions/labels within the same person (e.g. different moods, different cognitive loads, medication state etc.). An AI algorithm then combines demographic features and any other externally-known information, such as technical input features of the devices used to record.

In another example, when the dataset comprises of one or multiple data points in a variety of people, some of whom may have a known medical diagnosis (between-subject paradigm), a digital platform (computer, cloud, server) receives audio samples and speech signal processing occurs, which include extraction of audio signals under different conditions that is similar across all participants (e.g. mood, cognitive state) and participant group association (e.g. patient or control). An AI algorithm then combines demographic features and any other externally-known information, such as technical input features of the devices used to record.

The present invention may provide a system and method to classify physiological state, including symptoms of neurological disorder or neuropsychiatric disorder in a subject. The physiological states classified are preferably those which are generally obtained through subjective means from the subject including without limitation pain, stress, anxiety or sedation.

Accordingly, the physiological state determined by the analysis module may relate to one or more of: pain, dizziness, stress, anxiety, alertness, fatigue or sedation. For example, the physiological state may be a level of pain experienced by the subject, a level of alertness, fatigue or sedation of the subject, a level of anxiety or stress experienced by the subject.

Alternatively, or additionally, the physiological state determined by the analysis module may relate to a neurological or neuropsychiatric disorder. For example, the physiological state may be a likelihood that the subject suffers from a particular neurological or neuropsychiatric disorder.

Non-limiting examples of neurological or neuropsychiatric diseases, disorders or conditions referenced herein includes without limitation brain cancers, dementia, mild cognitive impairment, epilepsy, Alzheimer disease, Parkinson disease, multiple sclerosis, depression, schizophrenia, ADHD, PTSD, bipolar disorder, tic disorders (including Tourette's syndrome), OCD, anxiety disorders (including phobias and social anxiety disorder), Autism Spectrum Disorder, addiction, eating disorders, neuropathy, aphasia.

However, the person skilled in the art would appreciate that the terms neurological disease and/or neurological disorder encompass over a thousand medically-acknowledged conditions and, further, that the boundary between neurological and neuropsychiatric conditions can overlap. The World Health Organisation's International Statistical Classification of Diseases and Related Health Problems 10th Revision (ICD-10)-WHO Version for; 2016 Chapters V (mental and behavioural disorders) and VI (diseases of the nervous system) respectively provides a listing of such neuropsychiatric disorders (Chapter V thereof) and neurological disorders (Chapter VI thereof).

As used herein, pain may be a symptom of other underlying conditions whether neurological, neuropsychiatric or otherwise or may be a chronic pain condition. The chronic pain condition may be due to known or suspected causes such as arthritis, fibromyalgia, (lower-)back pain, migraines, other musculoskeletal problems, diabetes, nerve damage, Crohn's disease, chronic fatigue syndrome, irritable bowel syndrome, or cancer. The outputs of the invention can take the form of a risk score or report.

Several embodiments of the present invention will now be described to illustrate example uses of the systems and methods described above. These examples are intended to demonstrate the range of possible uses that can be made and are not to be considered in any way limiting the uses that could be made of the present invention. The uses set out in the examples below can be modified to suit specific needs of a particular user or neurological condition.

Example 1—Remote Monitoring Via Telephone, Mobile or Web

In one embodiment of the invention, the invention is embedded into a remote system used to monitor a patient with a neurological or neuropsychiatric condition. This will benefit patients who live far from a medical check-in post, may be on a waiting-list for treatment, may not require frequent in-person assessments, or may not be physically or mentally capable of traveling for in-person assessments. For example, patients with depression and low literacy frequently miss clinic appointments (Miller-Matero et al., 2016). Reminder systems such as pre-appointment telephone calls, email and via web-based electronic health records have been found to effectively increase adherence to clinic appointments, diagnosis and treatment (e.g. Liu et al., 2014; Gurol-Urganci et al., 2013).

The patient will receive a phone call, email or notification on a mobile device at regular time intervals, determined and pre-set based on medical records or requested by the patient's care team. The call, email and notification on the mobile device will all link to an embodiment of the invention hosted on a cloud-based server. The front-end module will present a set of cognitive tests to the patient, which can be specifically selected to minimise time constraints and maximise clinically informative voice features. The patient's responses will be recorded and processed via the speech module (parsing, feature extraction, feature normalisation) and AI back-end. The AI then outputs feedback to the patient acknowledging completion of monitoring, notifies them of the next session, and provides optional feedback on performance. The AI simultaneously outputs to a designated clinical team or medical health records a summary of performance, physiological state and disease score based on the AI computations.

This preferred embodiment will significantly improve disease progression monitoring; reduce clinician time spent on conducting routine monitoring tests, thus freeing time for delivering interventions; improve adherence to medication/hospital appointments; and provide a patient-centred medical care model. The added value of the present invention over prior art is that the active modulation of cognitive load in the front-end task delivery module will prevent any patients from manipulating their symptom or disease reports.

Example 2—Repeat Prescription System

In another preferred embodiment of the invention, a telephone or web-based system incorporates the present invention and is used to decide if a patient qualifies for a repeat prescription. For example, patients with chronic pain often require opioid drugs, where physical dependency and addiction are common side-effects. Such cases require close monitoring of prescription and pain symptoms. Currently, there is no objective measure for pain in the prior art and repeat prescription assessments are based on patient self-reports of their pain. Such subjective self-report may be exaggerated to sustain an addiction.

When a patient requests a repeat prescription over the telephone or the internet (e.g. through their electronic health records), the front-end module will present a set of cognitive tests to the patient, specifically selected to be sensitive to pain. Varying the cognitive load of the task, and thus, increasing mental effort and engagement required to successfully perform the task, the system makes it hard to impossible for a patient to fake pain signals in the voice. The patient's responses will be recorded and processed via the speech module (parsing, feature extraction, feature normalisation) and AI back-end. The AI then outputs feedback to the patient acknowledging completion of assessment. The AI simultaneously generates an output to the pharmacist and/or designated clinical team and/or medical health records a pain score for that patient. The ultimate decision to repeat prescription lies with the clinical team.

Example 3—Post-Operative Discharge From In-Patient Care

In a further preferred embodiment, the present invention may serve as an in-patient bed-side tool to determine when a patient is ready to be discharged from the hospital after surgery. For example, patients may be keen to get home as soon as possible after surgery, but may not be ready to do so if they suffer effects such as sedation, dizziness, and pain, which they might hide on purpose to be discharged. Alternatively, there may be scenarios when a patient does not want to be discharged from care, and may exaggerate symptoms on purpose.

The invention can be presented via a small device on the patient's bedside table, such as a smartphone, Amazon Echo® or Google Home®. The patient will be tested before surgery, and at several intervals post-surgery. The front-end task presentation module will present a set of cognitive tests, specifically selected for their sensitivity to effects of sedation, dizziness and pain. The tests will vary in their cognitive load to reach a threshold at which the patient performs the task successfully. The patient's responses will be recorded and processed via the speech module (parsing, feature extraction, feature normalisation) and AI back-end. The AI then outputs feedback to the patient acknowledging completion of assessment and whether the patient is ready for discharge. The AI simultaneously generates an output to the designated clinical team a summary of performance, including how the threshold for the patient compares to others and their own pre-surgery threshold.

Accordingly, the analysis module 3 is configured to determine whether or not the subject is fit to be discharged from hospital after treatment for a medical condition.

Example 4—Monitor Effects of Intervention

Another embodiment of the invention incorporates the system as described in this invention as an objective assessment of the effectiveness of non-medication based interventions, such as physiotherapy, psychotherapy, or digital health app. Currently the effectiveness of these types of interventions are assessed using subjective self-report measures of pain, mood, and quality of life. Such measures are sensitive to person-specific characteristics such as motivation, personal affect towards therapist, and the placebo effect. The present invention provides an objective method of measuring the effectiveness of intervention by comparing participant's performance and voice features before and after intervention (and set points in between).

The front-end task delivery module will present a set of cognitive tests, specifically selected for their sensitivity to effects of pain. The tests will vary in their cognitive load, and thus mental effort required to complete the tasks successfully. This method maximises voice features associated with pain and mental effort. The patient's responses will be recorded and processed via the speech module (parsing, feature extraction, feature normalisation) and AI back-end. The AI then outputs feedback to the patient acknowledging completion of assessment and whether the patient is ready for discharge. The AI simultaneously generates an output to the therapist a summary of performance, including how the threshold for the patient compares to previous sessions. Therapists may find this information useful to better personalise their intervention strategies.

Example 5—Safety Control

In a further preferred embodiment of the present invention, the system is used as a safety control system for use in relation to individuals who are employed in particular high-risk occupations, such as air traffic control, pilots, surgeons, heavy machinery operators, or in relation to devices and vehicles that require a level of alertness to operate, like a car, tram, train.

Before operation of high-risk procedures and heavy-duty machinery, the person is prompted to perform a set of short cognitive tasks, specifically selected to be sensitive to pick up changes in alertness and sedation. These tasks will be presented varying in cognitive load until a threshold is reached at which the person performs the task successfully. The individual's responses will be recorded and processed via the speech module (parsing, feature extraction, feature normalisation) and AI back-end. The AI then performs computations comparing the person's cognitive threshold and voice features related to cognitive performance deltas to predetermined thresholds deemed acceptable to perform high-risk procedure or occupation. The AI will feedback to the person if he/she is considered fit to proceed. The AI simultaneously generates an output to the employer or supervisor if the person's threshold falls below predetermined threshold.

Accordingly, the analysis module 3 may be configured to determine whether or not the subject is fit to perform high risk activity, wherein the high risk activity is selected from a group comprising: air traffic control, piloting an aircraft, performing surgery, operating heavy machinery, driving a car a tram or a train.

Example 6—General Consumer Use

Another envisioned embodiment for the present invention is the embedding of this invention into a person-centred self-help system. For example, a person uses an application on a portable device (smartphone, tablet, electronic watch, or even the telephone) which uses the present invention to monitor cognitive state, disease progression or medication over time. The output of the AI back-end (e.g. risk score, change in disease state, medication effect) could be set up to link to a 'alert' or 'feedforward' system that send both feedback to the user (for self-monitoring purposes) as well as to other parties specified by the user. These can be their clinical team, people responsible for their care, or link to other applications in the art that provide intervention and advice. For example, if the present invention establishes that the user is experiencing high levels of pain that negatively impact their cognitive function, this could 1) alert the user to consider taking additional medication (if within the remit of their care plan), 2) provide advice on self-management strategies like meditation, cognitive coping, and/or 3) record this as a time-point entry into a 'pain diary' for the clinical care team (where applicable).

Furthermore, the AI embedded within the present invention can be further developed to 'actively' learn to select which subsequent tasks to present to the user depending on responses given on screening questionnaires, demographic data and/or preceding tasks. For example, a user of a smartphone may call the front-end module via a health app. The front-end module then asks the user asked for some demographic information (or derives this information from the health app's API). This information is recorded and parsed to the AI, which computes a risk for certain symptoms by comparing the user's information to a database of other user demographics. The AI then selects a set of tasks that are most sensitive to pick up disease symptoms the user is at high risk for. This is presented to the user through the front-end module. User responses will be recorded and processed via the speech module (parsing, feature extraction, feature normalisation) and AI back-end. The AI then performs computations comparing the person's voice features related to cognitive performance deltas to their previous performance. The AI will alert the user if further action should be considered (like medication, or self-help strategies). The AI simultaneously generates an output to a designated care person.

Example 7—Clinical Trials Use in Assessing the Safety or Efficacy of a Treatment A further application of the invention is in clinical trials to assess the safety or efficacy of a treatment. Clinical trials are designed around objective endpoints to determine the safety and/or efficacy of a treatment. Currently, the assessment of cognitive function may be influenced by subjective outcomes (for example, pain, quality of life), subject motivation or training effects. The invention may be applied to provide improved objective determination of the impact of a treatment on cognitive function to assess the toxicity or efficacy of treatments in clinical trials. The invention provides a means of improving objective endpoints relating to self-diagnosed symptoms (such as pain or anxiety) or effects on cognitive function (such as memory or learning ability).

In a preferred embodiment, the invention is applied in a clinical trial to determine the efficacy of a treatment for pain.

In a further preferred embodiment, the invention is applied to determine whether a treatment results in adverse reactions with regard to the cognitive function of patients. The cognitive function to be assessed in the clinical trials may be auditory memory, working memory, associative learning ability, verbal fluency, verbal reasoning, emotion recognition, oral motor skills, processing speed and associated changes in these domains of cognitive function derived from the voice features extracted from the patients' testing sessions.

In certain embodiments, speech samples are collected from patients using a microphone in a telephone system, which may be a smartphone, and thus enabling monitoring of patients outside of the clinic.

The analysis module 3 may compare the physiological state of the subject to a baseline which includes specific population data for a neurological disorder, wherein the disorder is selected from a group of disorders comprising: pain, brain cancers, dementia, mild cognitive impairment, epilepsy, Alzheimer disease, Parkinson disease, multiple sclerosis, depression, schizophrenia, ADHD, PTSD, bipolar disorder, tic disorders (including Tourette's syndrome), OCD, anxiety disorders (including phobias and social anxiety disorder), Autism Spectrum Disorder, addiction, eating disorders, neuropathy, aphasia. The analysis module 3 may be configured to determine the safety or effectiveness of a treatment for pain, brain cancers, dementia, mild cognitive impairment, epilepsy, Alzheimer disease, Parkinson disease, multiple sclerosis, depression, schizophrenia, ADHD, PTSD, bipolar disorder, tic disorders (including Tourette's syndrome), OCD, anxiety disorders (including phobias and social anxiety disorder), Autism Spectrum Disorder, addiction, eating disorders, neuropathy, aphasia.

The present invention may provide a measure of the success of a clinical intervention. After performing a first assessment of the physiological state of the subject using the above described systems, a clinician may make an intervention (e.g. change the dosage of medication or provide physical therapy or any other intervention described above). After an appropriate period of time (depending on the intervention) a second assessment the physiological state of the subject using the above described systems. Accordingly, the invention allows a change in the physiological state to be determined. Thus the invention can provide measure of the success of a clinical intervention.

REFERENCES

Andersson, G. et al. (2002) 'Effect of cognitive load on postural control', Brain Research Bulletin. Elsevier, 58(1), pp. 135-139. doi: 10.1016/S0361-9230(02)00770-0.

Eyben, F., Weninger, F., Gross, F., & Schuller, B. (2013) Recent Developments in openSMILE, the Munich Open-Source Multimedia Feature Extractor, In Proc. ACM Multimedia (MM), Barcelona, Spain, ACM, ISBN 978-1-4503-2404-5, pp. 835-838. doi:10.1145/2502081.2502224

Fusaroli, R. et al. (2017) Is voice a marker for Autism spectrum disorder? A systematic review and meta-analysis, Autism Research, 10(3), pp. 384-407. doi: 10.1002/aur.1678.

Gurol-Urganci I., de Jongh T., Vodopivec-Jamsek V., Atun R., Car J. (2013) Mobile phone messaging reminders for attendance at healthcare appointments. Cochrane Database of Systematic Reviews 2013, Issue 12. Art. No.: CD007458.DOI: 10.1002/14651858.CD007458.pub3

Huang, X., Acero, A. and Hon, H. (2001) Spoken Language Processing: A guide to theory, algorithm, and system development. Prentice Hall.

Johnstone T. (2001) PhD Thesis. University of Western Australia. Accessed via http://brainimaging.waisman.wisc.edu/~tjohnstone/Thesis.pdf Lautenbacher, S. et al. (2017) 'Phonetic Characteristics of Vocalizations during Pain', Pain Reports, 2(e597), pp. 1-5.

Marquard, C. et al. (2017) 'Speak, Think , Act: A phonetic analysis of the combinatorial effects of respiratory mask , physical and cognitive stress on phonation and articulation', MSc Thesis. Accessed via https://www.researchgate.net/publication/315892441_Speak_Think_Act_A_phonetic_analysis_of_the_combinatorial_effects_of_respiratory_mask_physical_and_cognitive_stress_on_phonation_and_articulation Miller-Matero, L. R., Clark, K. B., Brescacin, C., Dubaybo, H. & Willens, DE (2016) Depression and literacy are important factors for missed appointments, Psychology, Health & Medicine, 21:6, 686-695, DOI:10.1080/13548506.2015.1120329

Nevler, N. et al. (2017) 'Automatic measurement of prosody in behavioral variant FTD', pp. 1-8. Oshrat, Y. (2014) The Fingerprints of Pain in Human Voice (Thesis, The Open University of Israel Computer Science Division)

Place et al (2017) Behavioral Indicators on a Mobile Sensing Platform Predict Clinically Validated Psychiatric Symptoms of Mood and Anxiety Disorders. J Med Internet Res. 19(3):e75 doi: 10.2196/jmir.6678

Tsai, F. S. et al. (2016) 'Toward development and evaluation of pain level-rating scale for emergency triage based on vocal characteristics and facial expressions', Proceedings of the Annual Conference of the International Speech Communication Association, INTERSPEECH, 8-12-NaN-2016, pp. 92-96. doi: 10.21437/Interspeech.2016-408.

Vogel, A. P., Fletcher, J. and Maruff, P. (2010) 'Acoustic analysis of the effects of sustained wakefulness on speech', The Journal of the Acoustical Society of America. Acoustical Society of America, 128(6), pp. 3747-3756. doi: 10.1121/1.3506349.

Zhang, H.-H. et al. (2016) 'Classification of Parkinson's disease utilizing multi-edit nearest-neighbor and ensemble learning algorithms with speech samples.', Biomedical engineering online. BioMed Central, 15(1), p. 122. doi: 10.1186/s12938-016-0242-6.

The invention claimed is:

1. A mobile computer device configured to perform prediction of a physiological state of a subject, the subject being a user of the mobile computer device, the physiological state being a level of pain experienced by the subject, a level of alertness, fatigue or sedation of the subject, or a level of stress or anxiety experienced by the subject, the mobile computer device comprising:
   one or more processors;
   a user interface device operatively coupled to the one or more processors;
   a microphone operatively coupled to the one or more processors;
   a first memory operatively coupled to the one or more processors, the first memory storing a plurality of cognitive tasks requiring a spoken response from the subject, each of the plurality of cognitive tasks associated with a cognitive load, and a plurality of sets of instructions for performing each of the plurality of cognitive tasks;

a second memory coupled to the one or more processors, and storing processor executable instructions, whereby:

the one or more processors are configured to:
  generate a sequence comprising respective successive cognitive tasks selected to have systematically varying different associated cognitive load, wherein the different associated cognitive load relates to one or more aspects of cognition selected from: working memory, short term auditory memory, associated learning ability, verbal reasoning ability, sustained attention, and auditory information processing,
  control the user interface device to communicate instructions for performing each of the plurality of cognitive tasks in the sequence to the subject,
  control the microphone to receive one or more audio signals comprising spoken responses to each of the plurality of cognitive tasks in the sequence by the subject, related to different cognitive loads,
  store the audio signals in a memory, and
  receive task performance signals related to each of the different cognitive loads,
for each one of the successive cognitive tasks in the sequence, the one or more processors are configured to:
  analyze the audio signals and the task performance signals for each of the different cognitive loads to determine speech characteristics of the spoken responses by the subject, by detecting portions of the spoken responses that correspond to each of the different cognitive loads, and
  calculate respective values associated with different speech characteristics, the different speech characteristics comprising at least two of: pitch, intensity, formant frequencies, glottal flow, speech duration, speech rate, and voice quality,
for the successive cognitive tasks in the sequence, the one or more processors are configured to:
  extract acoustic features corresponding to the different speech characteristics,
  calculate delta values for each of the acoustic features from higher cognitive load tasks to lower cognitive load tasks of the different cognitive loads,
  compare the respective values to the delta values, to determine speech characteristics related to a current physiological state of the subject, and
  thereby cancelling out speech characteristics related to task conditions but not the speech characteristics related to the current physiological state of the subject, to create a comparison, and
the one or more processors are configured to:
  perform a prediction of the current physiological state of the subject based at least in part on the speech characteristics related to the current physiological state within portions of the audio signals by using artificial intelligence/machine learning (AI/ML) based on training data relating human generated audio signals to a physiological state of a human, the physiological state of the human being a level of pain experienced by the human, a level of alertness, fatigue or sedation of the human, or a level of stress or anxiety experienced by the human, and
  output a determination, based on the prediction, of the physiological state of the subject comprising a level of pain experienced by the subject, a level of alertness, fatigue or sedation of the subject, or a level of stress or anxiety experienced by the subject and communicate the output to at least one of the subject via the user interface device or a clinical team, medical health record, or pharmacist.

2. The mobile computer device of claim 1, wherein the mobile computer device further comprises an automatic speech recognition system configured to analyze each of the task performance signals creating an analysis, compare results of the analysis with a pre-stored expected result creating a second comparison, and allocate a cognitive performance score to a performance of the subject on each of the plurality of cognitive tasks based on the second comparison, and determine the physiological state of the subject based at least in part on the cognitive performance score.

3. The mobile computer device of claim 2, wherein the one or more processors are further configured to: select a set of information relating to a next task based on the cognitive performance score corresponding to a preceding task, wherein, optionally if the cognitive performance score corresponding to the preceding task is lower than a predetermined threshold score, generating the next task to have an associated cognitive load lower than the cognitive load associated with the preceding task and if the cognitive performance score for the preceding task is higher than a predetermined threshold score, generating a next successive task so as to have an associated cognitive load higher than the cognitive load associated with the preceding task and if the cognitive performance score for the preceding task is determined to be an outlier, the next successive task is generated so as to have an associated cognitive load substantially similar to the cognitive load associated with the preceding task, wherein the one or more processors are configured to present to the subject with information based on the cognitive performance score for the preceding task, before communicating a set of information relating to the next successive task.

4. The mobile computer device of claim 1, wherein the one or more processors is further configured to determine the physiological state of the subject based on a subset of the speech characteristics of an audio signal corresponding to the spoken response, the subset being selected based on each of the plurality of cognitive tasks corresponding to the spoken response.

5. The mobile computer device of claim 1, wherein the one or more processors is further configured to detect speech features in an audio signal corresponding to a spoken response including full utterances, sentences, words and syllables, to determine the speech characteristics based on a subset of the speech features selected based on each of the plurality of cognitive tasks associated with the spoken response.

6. The mobile computer device of claim 1, further comprising a speaker configured to produce sound that communicates trial tasks, or a display device configured to visually communicate the trial tasks.

7. The mobile computer device of claim 1, wherein each of the plurality of cognitive tasks may be one of a plurality of types of cognitive tasks, wherein the plurality of types of cognitive tasks include: a forward verbal digit span, a backward verbal digit span, verbal paired associates learning, non-word verbal paired associates learning, verbal list learning, sentence repetition, semantic category verbal fluency, phonological verbal fluency, similarity recognition, verbal emotion recognition, sustained phonation, diadochokinesis, paced auditory serial addition, serial subtraction, familiar sequences, or a verbal questionnaire.

8. The mobile computer device of claim 1, wherein some or all cognitive tasks in the sequence of the successive cognitive tasks are different trials of a same type of cognitive task.

9. An apparatus comprising:
- a microphone configured to receive a first audio signal comprising a spoken response to a first cognitive task associated with a first cognitive load and a first testing environment;
- a processor configured to extract first speech characteristics from the first audio signal including one or more of pitch, intensity, formant frequencies, glottal flow, speech duration, speech rate, and voice quality, and to determine one or more first values associated with the first speech characteristics;
- the microphone configured to receive a second audio signal comprising a spoken response to a second cognitive task associated with a second cognitive load and first testing environment;
- the processor configured to extract second speech characteristics from the second audio signal including one or more of pitch, intensity, formant frequencies, glottal flow, speech duration, speech rate, and voice quality, and to determine one or more second values associated with the second speech characteristics; and
- the processor configured to compare the first values associated with the first speech characteristics to the second values associated with the second speech characteristics to determine an effect of cognitive load on a spoken response while maintaining a constant testing environment.

10. The apparatus of claim 9, wherein the processor is configured to use the determined effect of cognitive load on a spoken response to determine a physiological state of a patent.

* * * * *